United States Patent [19]
Colella et al.

[11] 3,943,173
[45] Mar. 9, 1976

[54] 3-ALKYLAMINO-ALPHA-AMINOMETHYL-4-HYDROXYBENZYL ALCOHOLS

[75] Inventors: Donald F. Colella, Philadelphia, Pa.; Carl Kaiser, Haddon Heights, N.J.

[73] Assignee: SmithKline Corporation, Philadelphia, Pa.

[22] Filed: Nov. 22, 1972

[21] Appl. No.: 308,867

[52] U.S. Cl. ...... 260/570.6; 260/343.7; 260/471 A; 260/501.11; 260/501.17; 260/501.12; 260/501.19; 260/562 R; 260/592; 424/280; 424/316; 424/330
[51] Int. Cl.² .......................................... C07C 91/22
[58] Field of Search....... 260/570.6, 501.11, 501.19, 260/501.17, 501.12, 343.7; 424/330

[56] References Cited
UNITED STATES PATENTS

| | | | |
|---|---|---|---|
| 2,393,820 | 1/1946 | Schnider | 260/570.6 |
| 3,818,101 | 6/1974 | Baile et al. | 424/330 |

*Primary Examiner*—Robert V. Hines
*Attorney, Agent, or Firm*—Stuart R. Suter; Alan D. Lourie; William H. Edgerton

[57] ABSTRACT

A series of 3-alkylamino-α-substituted aminomethyl-4-hydroxybenzyl alcohols are prepared. These compounds are β-adrenergic stimulants, in particular as bronchodilators.

6 Claims, No Drawings

3-ALKYLAMINO-ALPHA-AMINOMETHYL-4-HYDROXYBENZYL ALCOHOLS

This invention relates to substituted benzyl alcohols which show useful pharmacodynamic activity, especially as β-ardrenergic stimulants. In particular, the compounds have relatively greater activity on respiratory smooth muscle than on cardiac smooth muscle.

The compounds of this invention are 3-alkylamino-α-aminomethyl-4-hydroxybenzyl alcohols which are represented by the following structural formula

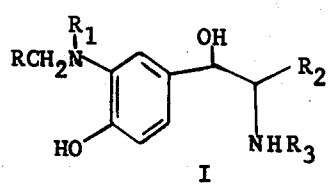

wherein
R and $R_1$ are each hydrogen or $C_1$–$C_4$ alkyl;
$R_2$ is hydrogen, methyl, or ethyl; and
$R_3$ is isopropyl, t-butyl, cyclobutyl, 1-(p-hydroxybenzyl)ethyl, or 2-(p-hydroxybenzyl)isopropyl.

Compounds where R and $R_2$ are hydrogen, $R_1$ is hydrogen or methyl, and $R_3$ is t-butyl, cyclobutyl, isopropyl, 1-(p-hydroxybenzyl)ethyl, or 2-(p-hydroxybenzyl)isopropyl are the preferred compounds of this invention.

In general, the compounds are prepared as illustrated by the following sequence of reactions.

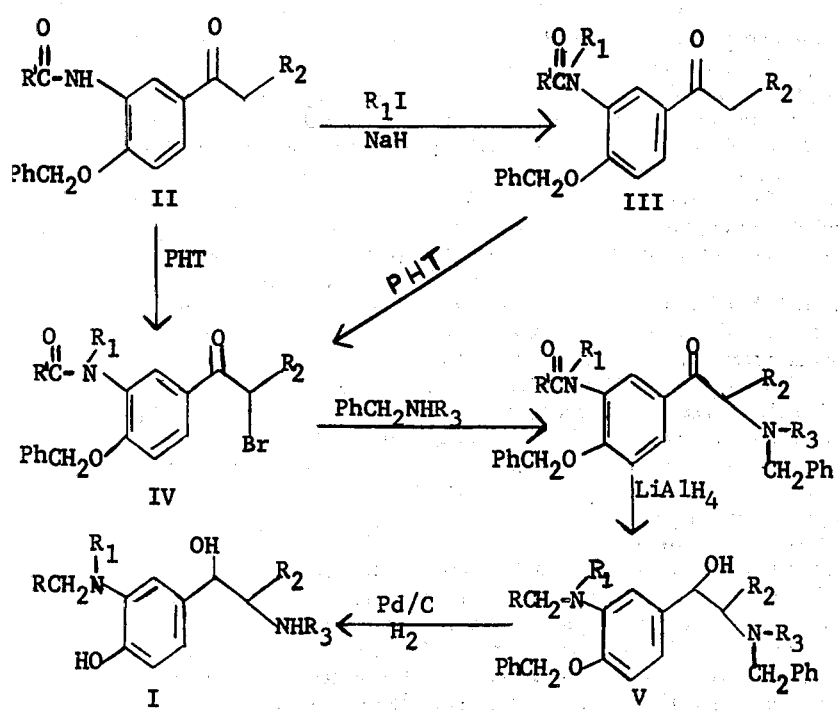

R' may be hydrogen, lower alkyl of 1 to 3 carbon atoms or an alcohol residue such as methoxy or ethoxy and R, $R_1$, $R_2$, and $R_3$ are as defined above.

Starting compound II is prepared by acylation of the appropriate aminobenzyloxyphenone by standard methods. The aminobenzyloxyphenones are known or prepared by known methods. For example, a 4-hydroxyphenone is nitrated with nitric acid at −20° to −30°C to give a 4-hydroxy-3-nitrophenone which is converted into a 4-benzyloxy-3-nitrophenone on treatment with benzyl chloride and a base such as potassium hydroxide or potassium carbonate. Reduction of the nitro group by standard methods, such as Raney nickel and hydrazine hydrate, platinum oxide and hydrogen, or sodium sulfhydrate, gives the aminobenzyloxyphenone.

Product compounds where $R_1$ is alkyl are prepared by first alkylating compound II to give compound III followed by bromination to the α-bromophenone, IV. The alkylation is conducted by standard methods, such as an alkyl halide and base. Product compounds, where $R_1$ is hydrogen, are brominated directly to give derivative IV. The bromination is effected using bromine, pyrrolidone hydrotribromide (PHT), or a similar reagent. Displacement of the bromine with the appropriate secondary benzylamine followed by reduction with lithium aluminum hydride gives the dibenzyl derivative of the compounds of this invention, V. Debenzlation by hydrogenolysis, preferably using palladium-on-carbon, gives the product compound I.

Compounds as defined by formula V are useful intermediates in the preparation of compound I and are therefore a part of this invention.

Due to the presence of an asymmetric carbon atom, compounds of this invention may be present as D or L optical isomers. In addition, when $R_2$ is not hydrogen, a second asymmetric center exists and *erythro* and *threo* diastereomers may be present. The resolution of the optical isomers may be done by standard methods. It is to be understood that all isomers, whether separated or in mixtures, are within the scope of this invention.

The compounds of this invention may be used in the form of a pharmaceutically acceptable acid addition salt having the utility of the free base. Such salts, prepared by well known methods, are formed from both inorganic and organic acids, such as maleic, fumaric, benzoic, ascorbic, pamoic, succinic, bismethylenesalicyclic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids.

The compounds of this invention may be administered in various conventional dosage unit forms such as tablets, capsules, injectables, aerosols, or the like, by incorporating the appropriate dose of the active compound with carriers according to accepted pharmaceutical practices.

The compounds of this invention are $\beta$-adrenergic stimulants which have direct bronchodilator activity with minimal cardiac stimulation. This selective $\beta$-stimulant activity is determined by two standard in vitro pharmacological test systems: (1) effect on spontaneous tone of guinea pig tracheal chain preparations as a measure of $\beta$-stimulant (direct relaxant) effect on airway smooth muscle, and (2) effect on spontaneously beating right atria of the guinea pig as a measure of $\beta$-stimulant effect on cardiac muscle. Compounds that show selective bronchodilating properties, as the compounds of this invention do, are active in test (1) at a dose lower than is required in test (2) thereby resulting in a positive separation ratio. Results of test (1) are reported as the dose which produces 50% of the maximum possible relaxation ($ED_{50}$). Test (2) results are reported as the dose which produces a 25% of the maximum possible increase in atrial contraction rate ($ED_{25}$).

A preferred compound of this invention is $\alpha$-(t-butylaminomethyl)-4-hydroxy-3-methylaminobenzyl alcohol which has an $ED_{50}$ of 0.000025 mcg/ml and an $ED_{25}$ of 0.0022 mcg/ml. These activities give an absolute separation ratio of 88. Another preferred compound is $\alpha$-(t-butylaminomethyl)-4-hydroxy-3-dimethylaminobenzyl alcohol which relaxes the spontaneous tone of guinea pig tracheal ring preparation at an $ED_{50}$ of 0.029 mcg/ml and increases the rate of contraction of guinea pig right atria at an $ED_{25}$ of 7.4 mcg/ml which results in an absolute separation ratio of 255.

A structurally related compound, $\alpha$-(t-butylaminomethyl)-4-hydroxy-3-aminobenzyl alcohol, is disclosed in Netherlands Pat. No. 85,197 as a bronchospasmolytic. Under the same in vitro tests, this compound showed an $ED_{50}$ of 0.0047 mcg/ml and an $ED_{25}$ of 0.026 mcg/ml or an absolute separation ratio of only 5.5. Also disclosed within this patent is $\alpha$-(isopropylaminomethyl)-4-hydroxy-3-aminobenzyl alcohol. This compound showed an $ED_{50}$ of 0.010 mcg/ml and an $ED_{25}$ of 0.022 mcg/ml, or an absolute separation ratio of 2.1 which again is much smaller than the ratios observed for the compounds of this invention.

The following examples are presented to illustrate preparation methods for specific compounds of this invention. These examples, however, should not be construed as a limitation of the scope of this invention since variations within the skill of the art will produce the compounds within the scope of this invention.

EXAMPLE 1

A solution of 3-amino-4-benzyloxyacetophenone (20.0 g, 0.083 mol) in ethyl formate (230 ml) was refluxed for 24 hours and then concentrated in vacuo. The residue was taken up in methylene chloride and washed with dilute HCl and saturated saline. The organic solution was dried and evaporated to a gum which on trituration with ether gave 4-benzyloxy-3-formamidoacetophenone, mp 120–122°.

To a stirred solution of 4-benzyloxy-3-formamidoacetophenone (60.3g, 0.224 mol) in dimethyl sulfoxide (270 ml) and under a nitrogen atmosphere was added sodium hydride as a 57% oil suspension (9.4g, 0.224 mol) in portions. The reaction was stirred until hydrogen evolution ceased and then was cooled with an ice bath. A solution of methyl iodide (35.8 g, 0.246 mol) in dimethyl sulfoxide (90 ml) was added dropwise to the cold solution. The reaction was stirred at room temperature for 15 minutes, heated at 55°–60° for 1 hour and then poured into ice water. The aqueous mixture was extracted with ethyl acetate. The dried extracts were evaporated to a residue which was triturated with ether and diluted with petroleum ether to give 4-benzyloxy-3-(N-methylformamido)acetophenone, mp 85–87°.

To a mixture of 4-benzyloxy-3-(N-methylformamido)acetophenone (37.5 g, 0.139 mol) and 2-pyrrolidone (11.8 g, 0.139 mol) in dry THF (1400 ml) was added dropwise PHT (69.0 g, 0.139 mol) in dry THF (1400 ml). The mixture was stirred at room temperature for 2 days. The salt was removed by filtration and the filtrate was evaporated to a residue which was dissolved in methylene chloride. The solution was washed with water, dried, decolorized, and evaporated to an oil which solidified. Recrystallization from ethyl acetate gave 4-benzyloxy-$\alpha$-bromo-3-(N-methylformamido)acetophenone, mp 108–113°.

A solution of the above $\alpha$-bromoacetophenone (10.86 g, 0.03 mol) and benzyl-t-butylamine (9.75 g, 0.03 mol) in acetonitrile (50 ml) was refluxed for 2 hours. The solution was cooled, diluted with ether (300 ml) and filtered. the filtrate was washed with water, dried, and concentrated to an oil. The oil was dissolved in ether (100 ml) and the solution was added dropwise to a suspension of LiAlH$_4$ (5.7 g, 0.15 mol) in ether (300 ml). The mixture was refluxed 6 hours and then the excess reagent was decomposed by the careful addition of water (6 ml) followed by 3% NaOH solution (24 ml). The mixture was filtered and the filtrate was evaporated to an oil, 4-benzyloxy-3-dimethylamino-$\alpha$-(benzyl-t-butylaminomethyl)benzyl alcohol. This product in ethanol (100 ml) was hydrogenated at room temperature and 65 psi using 10% Pd on carbon (3 g) as catalyst. Evaporation of the filtered mixture gave an oil which crystallized on trituration with ether to yield $\alpha$-(t-butylaminomethyl)-3-dimethylamino-4-hydroxybenzyl alcohol, mp 108°–110°.

EXAMPLE 2

A solution of 4-benzyloxy-60 -bromo-3-ethoxycarbonylaminoacetophenone (6.8 g, 0.0173 mol) (prepared as in U.S. Pat. No. 3,657,319) and benzyl-t-butylamine (5.22 g, 0.032 mol) in acetonitrile (50 ml) was refluxed for 1.5 hours, then cooled to 0°, diluted with ether, and filtered. The filtrate was washed with water, dried, and concentrated to an oil which was taken up in a minimal amount of ethanol. The solution was acidified with ethereal HCl and then was diluted with ether to give the solid hydrochloride salt. The salt was dissolved in water and the solution was made basic with NH$_4$OH and extracted with ether. The dried extracts were evaporated to an oil, α-(benzyl-t-butylamino)-4-benzyloxy-3-ethoxycarbonylaminoacetophenone.

This product was reduced first with LiAlH₄ and then hydrogen with 10% Pd on carbon as catalyst as described in example 1 to give α-(t-butylaminomethyl)-4-hydroxy-3-methylaminobenzyl alcohol.

EXAMPLE 3

Substitution of benzylisopropylamine in examples 1 and 2 for benzyl-t-butylamine and proceeding as described therein gives 3-dimethylamino-4-hydroxy-α-isopropylaminomethylbenzyl alcohol and 4-hydroxy-α-isopropylaminomethyl-3-methylaminobenzyl alcohol as products.

EXAMPLE 4

Following the procedures outlined in example 1, 4-benzyloxy-α-bromo-3-(N-methylforamido)acetophenone is condensed with N-benzyl-N-[1-(p-hydroxybenzyl)ethyl]amine to give, after the ensuing reductions, 3-dimethylamino-4-hydroxy-α-[1-(p-hydroxybenzyl)ethyl]benzyl alcohol.

Likewise, the use of N-benzyl-N-[1-(p-hydroxybenzyl)-ethyl]amine in example 2 gives, after the reductions, 4-hydroxy-α-[1-(p-hydroxybenzyl)ethyl]-3-methylaminobenzyl alcohol.

EXAMPLE 5

The reaction of 3-amino-4-hydroxypropiophenone according to the procedures of example 1 gives α-(1-t-butylaminoethyl)-3-dimethylamino-4-hydroxybenzyl alcohol.

Similarly, the use of 4-benzyloxy-3-ethoxycarbonylaminopropiophenone as starting material in example 2 yields α-(1-t-butylaminoethyl)-4-hydroxy-3-methylaminobenzyl alcohol.

EXAMPLE 6

Reacting 3-amino-4-benzyloxyacetophenone with ethyl acetate and then with ethyl iodide according to the procedures in example 1 gives 4-benzyloxy-3-(N-ethylacetamido) acetophenone. Using the ensuing reaction procedures of example 1, α-(t-butylaminomethyl)-3-diethylamino-4-hydroxybenzyl alcohol is obtained.

The use of 3-acetamido-4-benzyloxy-α-bromoacetophenone (prepared by bromination of 3-acetamido-4-benzyloxyacetophenone according to the procedure in example 1) as starting material in example 2 yields α-(t-butylaminomethyl)-3-ethylamino-4-hydroxybenzyl alcohol as final product.

We claim:

1. A compound of the formula

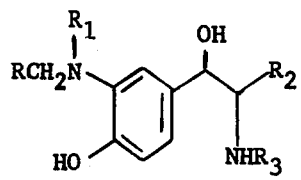

wherein

R and $R_1$ are each hydrogen or $C_1$–$C_4$ alkyl;
$R_2$ is hydrogen, methyl, or ethyl; and
$R_3$ is isopropyl, t-butyl, cyclobutyl,
  1-(p-hydroxybenzyl) ethyl, or 2-(p-hydroxybenzyl)-isopropyl or a pharmaceutically acceptable nontoxic salt thereof.

2. A compound as claimed in claim 1 where $R_2$ is hydrogen.

3. A compound as claimed in claim 2 where $R_1$ is hydrogen.

4. A compound as claimed in claim 2 where $R_3$ is t-butyl.

5. A compound as claimed in claim 4 being the compound α-(t-butylaminemethyl)-4-hydroxy-3-methylaminobenzyl alcohol.

6. A compound as claimed in claim 2 being the compound α-(t-butylaminemethyl)-3-dimethylamino-4-hydroxybenzyl alcohol.

* * * * *

UNITED STATES PATENT AND TRADEMARK OFFICE
CERTIFICATE OF CORRECTION

PATENT NO. : 3,943,173
DATED : March 9, 1976
INVENTOR(S) : Donald F. Colella and Carl Kaiser It is certified that error appears in the above-identified patent and that said Letters Patent are hereby corrected as shown below:

Column 4, line 57: "60-bromo" should read -- α-bromo --

Signed and Sealed this

Twentieth Day of July 1976

[SEAL]

Attest:

RUTH C. MASON
Attesting Officer

C. MARSHALL DANN
Commissioner of Patents and Trademarks